United States Patent [19]

Bacha

[11] Patent Number: 5,614,488
[45] Date of Patent: Mar. 25, 1997

[54] EPIDERMAL GROWTH FACTOR RECEPTOR TARGETED MOLECULES FOR TREATMENT OF INFLAMMATORY ARTHRITIS

[75] Inventor: Patricia A. Bacha, Hollis, N.H.

[73] Assignee: Seragen, Inc., Hopkinton, Mass.

[21] Appl. No.: 116,806

[22] Filed: Sep. 3, 1993

Related U.S. Application Data

[63] Continuation of Ser. No. 5,871, Jan. 15, 1993, abandoned, which is a continuation of Ser. No. 726,316, Jul. 5, 1991, abandoned.

[51] Int. Cl.$^6$ ............................................. A61K 38/00
[52] U.S. Cl. .............................. 514/2; 435/69.7; 536/23.4
[58] Field of Search .................... 435/69.7; 514/2; 536/23.4

[56] References Cited

U.S. PATENT DOCUMENTS

| | | | |
|---|---|---|---|
| 4,468,382 | 8/1984 | Bacha et al. | 424/177 |
| 4,545,985 | 10/1985 | Pastan et al. | 424/85 |
| 4,675,382 | 6/1987 | Murphy | 530/350 |
| 4,946,778 | 8/1990 | Ladner et al. | 435/69.6 |

OTHER PUBLICATIONS

Chaudhany et al PNAS 84:4538–4542 1987.
Yocum et al Abstract D98, p. S150, 54th Annual Meeting American College of Rheumatology Seattle, WA Oct. 1990.
Shaw et al., "Cytotoxic Properties of $DAB_{486}EGF$ and $DAB_{389}EGF$, Epidermal Growth Factor (EGF) Receptor–targeted Fusion Toxins", The Journal of Biological Chemistry, 266(31):21118–21124, (1991).
Williams et al., "Structure/Function Analysis of Interleukin-2-Toxin ($DAB_{486}$–IL–2)", The Journal of Biological Chemistry, 265(2):11885–11889, (1990).
Johnson et al., U.S. Department of Health and Human Services, U.S. Serial No. 401, 412.
Huse et al., Science 246:1275–1281, 1989.
Case et al., Proc. Natl. Acad. Sci. USA 86:287–291, 1989.
Zvaifler et al., The American Journal of Medicine 85:12–17, 1988.
Defeo–Jones et al., Molecular and Cellular Biology, 8:2999–3007, 1988.
Stunkel et al., Immunology 64:683–689, 1988.
Williams et al., Nucleic Acids Research 16:10453–10467, 1988.
Calderwood et al., Proc. Natl. Acad. Sci. USA 84:4364–4368, 1987.
Hwang et al., Cell 48:129–136, 1987.
Colombatti et al., The Journal of Biological Chemistry, 261:3030–3035, 1986.
Holoshitz et al., The Lancet 2:305–309, 1986.
Pappenheimer, Ann. Rev. Biochem. 46:69–94, 1977.
Uchida et al., The Journal of Biological Chemistry 248:3838–3844, 1973.
Hertel et al., The Journal of Biological Chemistry 260:12547–12553, 1985.
Moya et al., The Journal of Cell Biology 101:548–559, 1985.
Hoch et al., Proc. Natl. Acad. Sci. USA 82:1692–1696, 1985.
Amann et al., Gene 40:183–190, 1985.
Gray et al., Proc. Natl. Acad. Sci. USA 81:2645–2649, 1984.
Beguinot et al., Proc. Natl. Acad. Sci. USA 81:2384–2388, 1984.
Deleers et al., FEBS 160:82–86, 1983.
Maassen et al., Euro. J. Biochem. 134:327–330, 1983.
Beck et al., Gene 19:327–336, 1982.
Moynihan et al., Infection and Immunity, 32:575–582, 1981.
Uchiyama et al., The Journal of Immunology 126:1393–1397, 1981.
Trentham et al., The Journal of Experimental Medicine 146:857–868, 1977.

*Primary Examiner*—John Ulm
*Attorney, Agent, or Firm*—Fish & Richardson, P.C.

[57] ABSTRACT

The invention features a method for treating a patient having inflammatory arthritis, the method includes administering to the patient a molecule which is capable of specifically binding to an epidermal growth factor receptor expressed on a cell of the patient which contributes to the inflammatory arthritis of the patient, the molecule being capable of decreasing the viability of the cell.

14 Claims, 2 Drawing Sheets

EPIDERMAL GROWTH FACTOR RECEPTOR TARGETED MOLECULES FOR TREATMENT OF INFLAMMATORY ARTHRITIS

This is a continuation of application Ser. No. 08/005,871, filed Jan. 15, 1993, now abandoned; which is a continuation of 07/726,316, filed Jul. 5, 1991, now abandoned.

BACKGROUND OF THE INVENTION

The field of the invention is treatment of inflammatory arthritis.

Inflammatory arthritis is a family of arthritic diseases characterized by lymphokine-mediated inflammation of the joints. Inflammatory arthritis is often autoimmune in origin; examples include rheumatoid arthritis, psoriatic arthritis, and lupus-associated arthritis. The most common form of inflammatory arthritis is rheumatoid arthritis which occurs in approximately 1 percent of the population. Rheumatoid arthritis is characterized by persistent inflammation of the joints. Inflammation can eventually lead to cartilage destruction and bone erosion.

Stükel et al. (Immunology 64:683, 1988) report that a monoclonal antibody directed against the interleukin-2 receptor inhibits passively transferred adjuvant arthritis in rats (i.e., adjuvant arthritis induced by transfer of spleen cells from rats having adjuvant arthritis to naive rats), but is not effective in suppressing the development of adjuvant arthritis in rats.

Case et al. (Proc. Natl. Acad. Sci. USA 86:287, 1989) report that a cytotoxic interleukin-2-Pseudomonas exotoxin fusion protein administered prior to the establishment of overt clinical disease mitigates adjuvant-induced arthritis in rats.

Rapidly proliferating synovial cells are characteristic of inflammatory arthritis. It has been proposed that "factors produced by . . . macrophages and synovial fibroblasts in the joint lining that can influence one another in a resonating or paracrine manner" may play a role in rheumatoid arthritis (Zvaifler, Am. J. Med. 85 (supplement 4A):12, 1988).

There is evidence that rheumatoid arthritis synovial cells have twice as many receptors for epidermal growth factor as normal cells (Yocum et al., Abstract D98, pS150, 54th Annual Meeting American College of Rheumatology, Seattle, Wash. October, 1990).

SUMMARY OF THE INVENTION

In general, the invention features a method for treating a patient having inflammatory arthritis; the method includes administering to the patient a molecule which is capable of specifically binding to an epidermal growth factor receptor expressed on a cell of the patient which contributes to the inflammatory arthritis of the patient, the molecule being capable of decreasing the viability of the cell.

In preferred embodiments, the inflammatory arthritis is rheumatoid arthritis; the inflammatory arthritis is systemic lupus erythematosus-associated arthritis; and the inflammatory arthritis is psoriatic arthritis.

In other preferred embodiments, the molecule kills cells bearing the epidermal growth factor receptor; and the molecule is a hybrid molecule which includes a first and a second portion joined together covalently, the first portion includes a molecule capable of decreasing cell viability and the second portion includes a molecule capable of specifically binding to the epidermal growth factor receptor.

In more preferred embodiments, the second portion includes all or a binding portion of an antibody specific for the epidermal growth factor receptor; the second portion includes all or a binding portion of a ligand for the epidermal growth factor receptor; and the first portion includes a cytotoxin.

In still more preferred embodiments the ligand is epidermal growth factor; and the ligand is transforming growth factor alpha.

In more preferred embodiments, the cytotoxin is a fragment of a peptide toxin which is enzymatically active but which does not possess generalized eukaryotic receptor binding activity; the fragment of a peptide toxin includes fragment A of diphtheria toxin and enough of fragment B of diphtheria toxin to facilitate entry of the molecule into the cytosol of the cell; the molecule is $DAB_{486}EGF$; the molecule is $DAB_{486}TGF$-alpha; the molecule is $DAB_{389}EGF$; and the molecule is $DAB_{389}TGF$-alpha.

In other preferred embodiments, the molecule includes all or a binding portion of an antibody specific for the cell receptor; and the antibody is a complement activating antibody.

In a related aspect, the invention features a method of reducing bone erosion in a patient having inflammatory arthritis; the method includes administering to the patient a molecule which is capable of specifically binding to an epidermal growth factor receptor expressed on a cell of the patient which contributes to the inflammatory arthritis of the patient, the molecule being capable of decreasing the viability of the cell.

In more preferred embodiments the inflammatory arthritis is rheumatoid arthritis; the molecule is $DAB_{486}EGF$; and the molecule is $DAB_{389}EGF$.

In a related aspect, the invention features a method for reducing pain in a patient having inflammatory arthritis; the method includes administering to the patient a molecule which is capable of specifically binding to an epidermal growth factor receptor expressed on a cell of the patient which contributes to the inflammatory arthritis of the patient, the molecule being capable of decreasing the viability of the cell.

By "specifically binding" is meant that the molecule does not substantially bind to other cell receptors or cell surface proteins. By "reduces viability" is meant kills or interferes with proliferation. By "ligand" is meant a molecule which is capable of binding to a protein.

Other features and advantages of the invention will be apparent from the following description of the preferred embodiments thereof, and from the claims.

DETAILED DESCRIPTION

The drawings are first briefly described.

Drawings

Figure 1A:
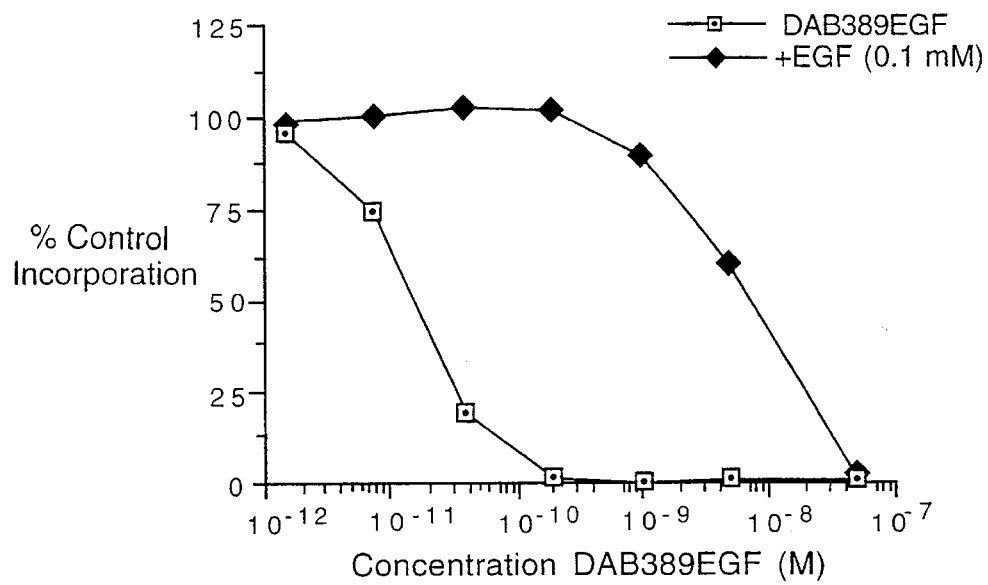
Figure 1B:
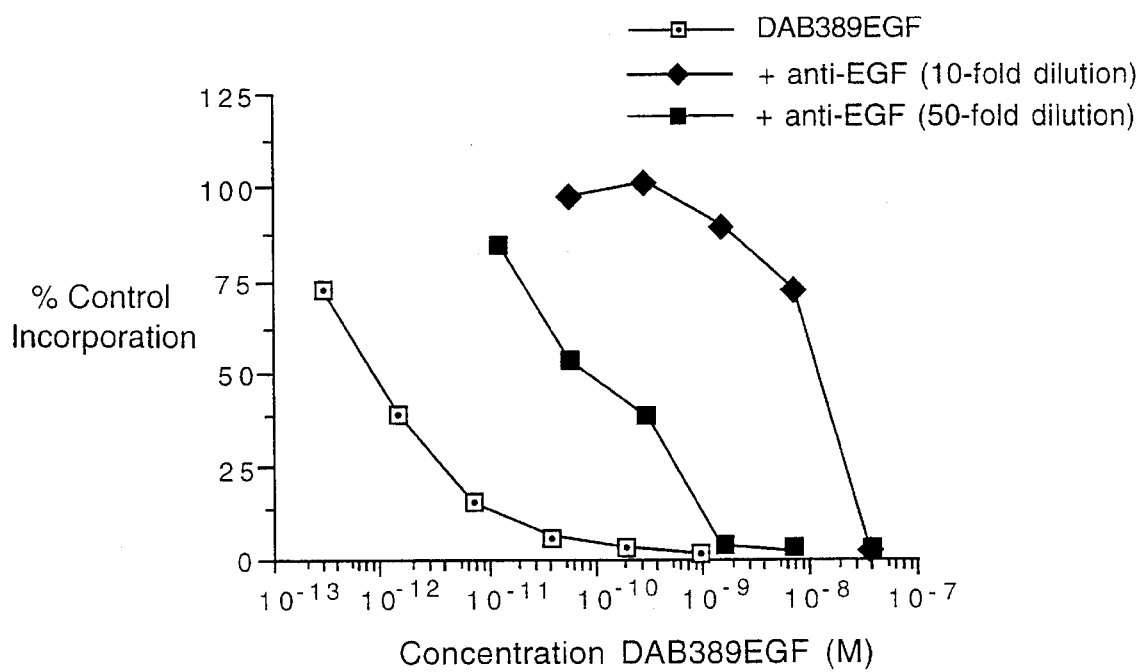
Figure 1C:
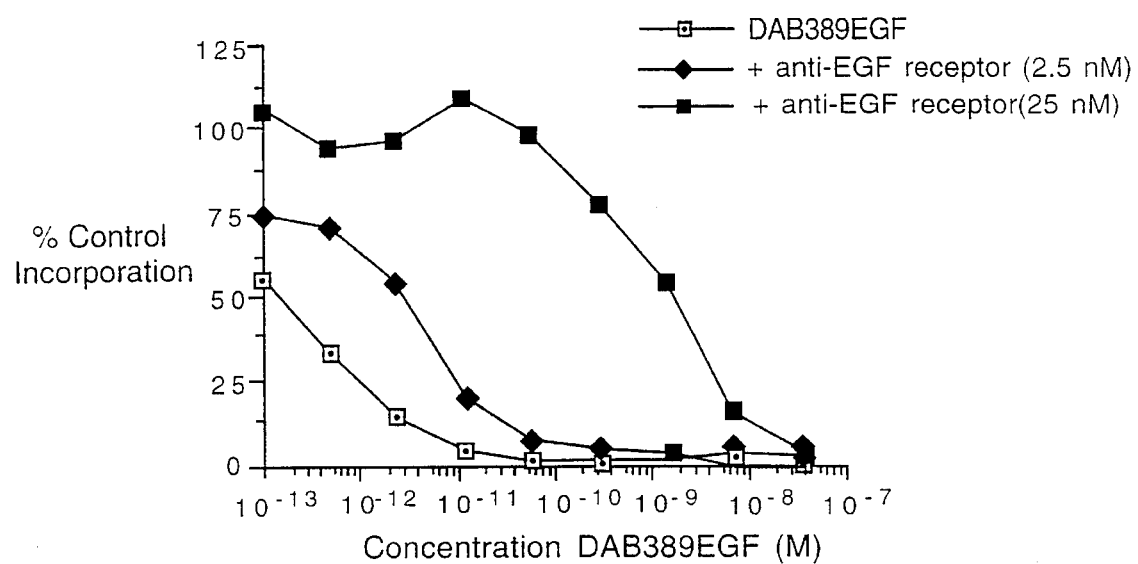

FIGS. 1A–1C is a set of graphs which depict the results of protein synthesis inhibition assays. Protein synthesis, as a percent of the control level, is plotted as a function of $DAB_{389}EGF$ concentration. In FIG. 1A $DAB_{389}EGF$ is added alone (open squares) or in the presence of 0.1 mM EGF (filled diamonds). In FIG. 1B $DAB_{389}EGF$ is added alone (open squares), in the presence of a 10-fold dilution of anti-EGF (filled diamonds) antibodies, or a 50-fold dilution of anti-EGF (filled squares) antibodies. In FIG. 1C $DAB_{389}EGF$ is added alone (open squares), in the presence of 2.5 nM anti-EGF receptor (filled diamonds) or in the presence of 25 nM anti-EGF receptor (filled squares).

Figure 2:
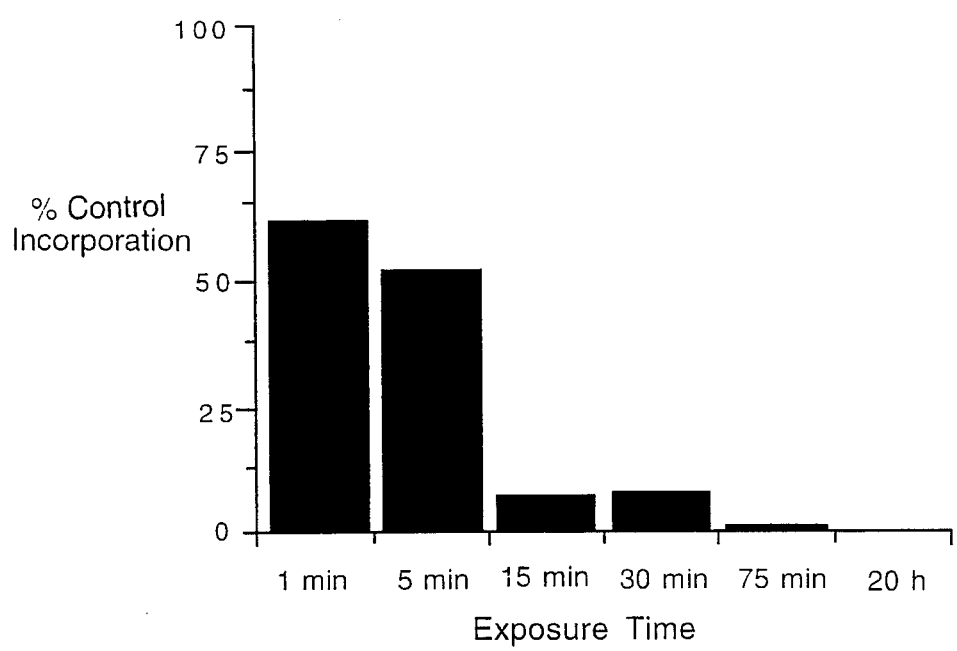

FIG. 2 is a graph which depicts the results of a protein synthesis inhibition assay. Protein synthesis, as a percent of the control level, is plotted as a function of time.

Epidermal Growth Factor—Targeted Cytotoxins for Treatment of Arthritis

Inflammatory arthritis is treated according to the invention by decreasing the viability of these rapidly proliferating synovial cells. EGF and derivatives of EGF are used to generate molecules which are capable of decreasing the viability of EGF receptor-bearing synovial cells. Described in detail below are methods for producing two examples EGF receptor targeted cytotoxins, $DAB_{389}EGF$ and $DAB_{486}EGF$. These molecules are fusion proteins in which EGF replaces the receptor binding domain of diphtheria toxin. Also described below are experiments which demonstrate that: (1) a lupine synovial fibroblast cell line (HIG-82) is sensitive to $DAB_{389}EGF$ at concentrations in the range of $5 \times 10^{-11}$ to $5 \times 10^{-10}$ M; (2) cell lines which express low levels of EGF receptor are insensitive to $DAB_{389}EGF$ and $DAB_{486}EGF$ at concentrations greater than $10^{-8}$ M; and (3) $DAB_{389}EGF$ is effective in alleviating the clinical features of arthritis in an animal model.

The EGF receptor-targeted cytotoxins described in detail below are only two specific examples of the EGF receptor targeted cytotoxins which are useful for treatment of inflammatory arthritis. For example, toxins other than diphtheria toxin may be fused to EGF, and monoclonal antibodies directed against the EGF receptor, can also be used in place of EGF to target the cytotoxin to EGF receptor expressing cells. Further, transforming growth factor alpha, which recognizes the EGF receptor, can also be used to target cells bearing the EGF receptor.

Production of $DAB_{486}EGF$ and $DAB_{389}EGF$

Oligonucleotides for construction of a synthetic EGF gene were synthesized using cyanoethyl phosphoramidite chemistry and were purified by preparative polyacrylamide gel electrophoresis (Current Protocols in Molecular Biology, Ausubel et al., eds., John Wiley & Sons, New York, 1989). Using standard DNA methodologies, the oligonucleotides were annealed and ligated to SmaI digested M13mp18. Single stranded DNA was prepared and sequenced by the dideoxy chain termination method. E. coli DH5a F' (BRL/ Gibco, Bethesda, Md.) was the host strain used for cloning and sequencing. One clone, M13EGF#2, was confirmed to have the correct EGF sequence and was used for subsequent cloning.

Plasmid pSI123 was the parental plasmid used to construct $DAB_{389}EGF$ and $DAB_{486}EGF$ expressing plasmids. pSI123 includes a $DAB_{486}IL-2$, a fusion protein composed of the first 485 amino acids of diphtheria toxin fused to amino acids 2 to 133 of human IL-2 (Williams et al., J. Biol. Chem. 265:11885, 1990; Williams et al., Nucl. Acids Res. 16:10453, 1988) and a pKK233-2 vector (Amann et al., Gene 40:183, 1985; Pharmacia, Piscataway, N.J.) modified as described below. The ampicillin resistance (bla) gene, the 5S rRNA gene and the tandem rrnB $T_1$ and $T_2$ transcriptional terminators from pKK233-2 were replaced with the neomycin resistance (neo) gene from Tn5 (Beck et al. Gene 19:327, 1982). The gene encoding $DAB_{486}IL-2$ was placed under control of the trc promoter by cloning into the unique NcoI site of pKK233-2. The trc promoter fusion was designed so that the amino terminus of $DAB_{486}IL-2$ would differ from that of mature diphtheria toxin only by the presence of the amino-terminal methionine. A synthetic DNA fragment containing the 28 base pair trpA transcriptional terminator was cloned downstream of the chimeric gene.

The vectors used to express $DAB_{486}EGF$ and $DAB_{389}EGF$ were constructed by replacing the IL-2 coding region from plasmid pSI123 with the EGF coding region from M13EGF#2. Specifically, for the expression of $DAB_{486}EGF$, M13EGF#2 was digested with SphI and ScaI and the 167 base pair fragment containing the synthetic EGF gene was ligated into plasmid pSI123 digested with SphI and ScaI to generate pSE1. For the expression of $DAB_{389}EGF$, plasmid pSE5 was constructed by digestion of pSE1 with ClaI and SphI and ligation of the 296 base pair ClaI/SphI fragment from plasmid pDW27 (Williams et al., supra) to the pSE1 vector backbone. DNA sequence and Western blot analyses confirmed that the plasmids encode $DAB_{486}EGF$ and $DAB_{389}EGF$.

$DAB_{389}EGF$ and $DAB_{486}EGF$ were produced by E. coli SCS1 (Stratagene, La Jolla, Calif.) transformed with the appropriate plasmid and grown in M9 minimal media supplemented with 5% (v/v) glycerol, casamino acids (10 mg/ml), thiamine (1 µg/ml) and neomycin sulfate (20 µg/ml) for 13 to 17 h at 30° C. When the cultures reached an absorbance of 1.3 at 550 nm, isopropyl-β-D thiogalactopyranoside was added to a final concentration of 0.35 mM and the cultures grown for an additional 90 min. The cells were concentrated, collected by centrifugation, and resuspended in PEST buffer (50 mM $KH_2PO_4$, pH 7.2, containing 10 mM EDTA, 750 mM NaCl, 0.1% TWEEN 20) to approximately 0.1 gram wet weight cells/ml. The cell slurry was then passed through a cell homogenizer (APV Gaulin, Model 15M 8TA) to lyse the cells. The cell lysate was clarified by centrifugation and filtered through a sterile 0.22 µm filter cartridge.

The cell lysate was next applied to an anti-diphtheria toxin immunoaffinity column equilibrated with PEST buffer. Following extensive washing of the column, the fusion toxin-containing fraction was eluted with a buffer containing guanidine hydrochloride. The immunoaffinity-purified protein was dialyzed overnight against 20 mM Tris, pH 8.0 containing 5 mM EDTA ($DAB_{486}EGF$) or 50 mM Hepes, pH 7.2 ($DAB_{389}EGF$). The dialyzed protein was applied to a Mono Q column (HR 5/5, Pharmacia, Piscataway, N.J.) for $DAB_{486}EGF$ or to a DEAE anion exchange column (Bio-Gel, DEAE-5-PW, 150×21.5 mm; BioRad Laboratories, Hercules, Calif.) equilibrated with 50 mM Hepes, pH 7.2 for $DAB_{389}EGF$. After washing with several column volumes of equilibration buffer, protein was eluted with a stepwise salt gradient. Fractions containing the purest $DAB_{486}EGF$ or $DAB_{389}EGF$, as analyzed by sodium dodecyl sulfate-polyacrylamide gel electrophoresis (SDS-PAGE), were pooled. The pool containing $DAB_{486}EGF$ or $DAB_{389}EGF$ was size fractionated by high pressure liquid chromatography. The column (TSK-Gel G3000PW, 600×21.5 mm; TosoHaas, Philadelphia, Pa.) was equilibrated with 10 mM sodium phosphate, pH 7.2, containing 150mM NaCl. Fractions containing the purest $DAB_{486}EGF$ or $DAB_{389}EGF$, as analyzed by SDS-PAGE, were pooled and used for the in vitro experiments described below.

Specificity of $DAB_{389}EGF$ Cytotoxicity

To demonstrate that the cytotoxic action of $DAB_{389}EGF$ is mediated selectively by the EGF receptor, cells of a cell line known to bear EGF receptor (A431 cells, American Type Culture Collection Accession Number CRL1555) were incubated with $DAB_{389}EGF$ in the presence of specific competitors of the EGF receptor. For each assay, cells were plated in triplicate wells of 96 well plates in the presence of 100 µl of serial dilutions of $DAB_{389}EGF$ in media with or without a competitive inhibitor. Following a 20 h incubation, protein synthesis was assayed by incubating the cells with L-[2,3,4,5-$^3$]leucine, 5 µCi/ml (110 Ci/mmole; ICN) in leucine-free Minimum Essential Medium (GIBCO, Bethesda, Md.) for 2 h. Adherent cells were detached from the wells with 0.25% trypsin, 0.02% EDTA (JRH Biosciences, Lenexa, Kans.) and harvested onto glass fiber filter mats. Radioactivity was determined by liquid scintillation counting and expressed as a percent of the incorporation by control cells incubated in media alone. Referring to FIG. 1, cells were incubated with $DAB_{389}EGF$ and 0.1 mM EGF (panel A, open squares), 10-fold dilution of rabbit antisera polyclonal anti-EGF antibody (panel B, diamonds), 50-fold dilution of rabbit antisera polyclonal anti-EGF antibody (panel B, filled squares), 25 nM monoclonal anti-EGF receptor (panel C, diamonds), or 2.5 nM monoclonal anti-EGF receptor (panel C, filled squares). For comparison, cells were incubated with $DAB_{389}EGF$ alone (panels A, B, and C, open squares). As shown by FIG. 1, $DAB_{389}EGF$ cytotoxicity was inhibited in a dose dependent manner by specific competitors of the EGF receptor (EGF, anti-EGF antibodies, and anti-EGF receptor antibodies). In a separate experiment, cells were incubated with $DAB_{389}EGF$ and the nonspecific competitors transferrin, anti-transferrin antibody, and anti-transferrin receptor antibody. These nonspecific competitors did not reduce the bioactivity of $DAB_{389}EGF$. These observations suggest that specific binding to the EGF receptor is required for effective inhibition of protein synthesis by $DAB_{389}EGF$.

Mechanism of $DAB_{389}EGF$ Cytotoxicity

Native diphtheria toxin intoxicates sensitive eukaryotic cells by inhibition of protein synthesis. This process occurs following binding of diphtheria toxin to its cellular receptor and internalization of the toxin by receptor mediated endocytosis. Acidification of the resulting endosome effects entry of fragment A into the cytosol and inactivation of elongation factor-2 (Moya et al., J. Cell Biol. 101:548, 1985). The EGF receptor also undergoes ligand mediated endocytosis and subsequent appearance in endosomes (Beguinot et al., Proc. Natl. Acad. Sci, USA 81:2384, 1984). To determine if the cytotoxicity of $DAB_{389}EGF$ is dependent upon the same pathway as diphtheria toxin, cells were incubated with $DAB_{389}EGF$ for 20 hr. in the presence of chloroquine (10 µM, Sigma, St. Louis, Mo.), a lysosomotropic compound which prevents acidification of endosomes, and the level of protein synthesis was measured as described above. As shown in Table 1, addition of chloroquine to A431 cells completely blocked the cytotoxicity of $DAB_{389}EGF$. Thus, it appears that, like diphtheria toxin, inhibition of protein synthesis by $DAB_{389}EGF$ requires passage of the molecule into an acidified vesicle.

TABLE 1

Inhibition of $DAB_{389}EGF$ cytotoxicity by Chloroquine

| | % of control Protein Synthesis* | |
| --- | --- | --- |
| $DAB_{389}EGF$ | −Chloroquine | +Chloroquine |
| 10 pm | 4 | 61 |
| 1 pm | 57 | 100 |

*Results for chloroquine + $DAB_{389}EGF$ treatment are relative to chloroquine treatment alone which reduced protein synthesis by 27%.

Following translocation into the cell cytosol, fragment A of diphtheria toxin catalyzes the cleavage of NAD and the covalent linkage of ADP-ribose to elongation factor-2. The ADP-ribosylation of elongation factor-2 results in inhibition of protein synthesis and ultimately cell death (Pappenheimer et al., Ann. Rev. Biochem. 46:69, 1977). To evaluate the mechanism by which $DAB_{389}EGF$ inhibits protein synthesis, A431 cells were incubated with $DAB_{389}EGF$ or diphtheria toxin and then assayed to quantitate the elongation factor-2 available for ADP-ribosylation, using a modification of the method of Moynihan et al. (Infect. Immunol 32:575, 1981). Briefly, cells were plated in triplicate wells of 24 plates and incubated with $DAB_{389}EGF$, diphtheria toxin (List Biological Laboratories, Campbell, Calif.) or media for 20 h. The cells were washed and incubated for 20 min at 37° C. with [adenylate-$^{32}$P]NAD, 25 µCi/ml (250 Ci/mmole; ICN, Costa Mesa, Calif.) in lysis buffer containing 10 mM Tris, 10 mM NaCl, 3mM $MgCl_2$, 10 mM Tris, 10 mM NaCl, 3 mM $MgCl_2$ 10 mM thymidine, 1 mM EGTA and 1% Triton X-100, pH 8 and 0.4 µg diphtheria toxin fragment A (purified by reverse phase HPLC from nicked diphtheria toxin). Trichloroacetic acid precipitable extracts were collected on glass fiber filters and radioactivity was quantitated to assess the percent of control levels of elongation factor-2 available for ADP-ribosylation. Referring to Table 2, both $DAB_{389}EGF$ and diphtheria toxin treatments reduced the level of available elongation factor-2 in A431 cells. This observation suggests that the cytotoxicity of $DAB_{389}EGF$ results from inactivation of elongation factor-2 through ADP-ribosylation in a manner similar to native diphtheria toxin.

TABLE 2

Elongation Factor 2 Available for ADP - Ribosylation

| Toxin | Concentration | % Control Level EF-2 Available for ADP - Ribosylation |
| --- | --- | --- |
| Diphtheria Toxin | 10 nM | <1 |
| | 1 nM | 17 |
| $DAB_{389}EGF$ | 10 nM | 13 |
| | 1 nM | 20 |

Specific Binding of $DAB_{389}EGF$ to the EGF Receptor

The ability of $DAB_{389}EGF$ to displace specific [$^{125}$I]EGF binding to A431 cells was assessed and compared to native EGF. Binding conditions had previously been established to provide maximum specific [$^{125}$I]EGF binding (>95%). Three separate experiments were performed to determine the molar concentration of competitor ($DAB_{389}EGF$ or EGF) required to displace 50% of the control [$^{125}$I]EGF binding (in the absence of competitor).

Briefly, cells plated in triplicate wells of 24 well plates were washed with Dulbecco's modified Eagle's medium containing 0.1% bovine serum albumin (binding media) and preincubated with 15 mM sodium azide and 50 mM 2-deoxyglucose in phosphate buffered saline for 1 h or with 0.1 mM phenylarsineoxide (Hertel et al., J. Biol. Chem. 260:1247, 1985) in binding media for 5 min to prevent EGF receptor internalization. The cells were washed and incubated for 1 h at 37° C. with 0.5 nM [$^{125}$I]EGF (ICN) in the presence of serial 2-fold dilutions of $DAB_{389}EGF$ or human EGF (Upstate Biotechnology, Lake Placid, N.Y.) or binding media alone. The cells were then washed extensively and solubilized in 1N NaOH. The amount of radioactivity bound to the cells was determined and expressed as a percent of control radioactivity incorporated by cells incubated with [$^{125}$I]EGF in binding media. DAB$_{389}$EGF was 15 to 30-fold less potent in displacing [$^{125}$I]EGF binding than native EGF. This finding may be explained by the fact that DAB$_{389}$EGF is a much larger molecule than EGF with a molecular weight almost 10-fold greater.

Kinetics of DAB$_{389}$EGF cytotoxicity

The minimum amount of time that cells must be exposed to DAB$_{389}$EGF to induce maximum inhibition of protein synthesis was determined by a modification of the cytotoxicity assay. A431 cells were incubated with DAB$_{389}$EGF (250 ng/ml) for varying amounts of time, washed extensively, and then incubated in media alone. The total incubation time was 20 h in each case. The cells were then radiolabeled to assess the extent of inhibition of protein synthesis. The percent of control radiolabel incorporation was compared to parallel cultures which were washed and incubated continuously with DAB$_{389}$EGF for 20 h. Referring to FIG. 2, only a 15 min exposure was required for DAB$_{389}$EGF to bind irreversibly to the EGF receptor of A431 cells.

To examine the kinetics of DAB$_{389}$EGF cytotoxicity, the amount of time required for DAB$_{389}$EGF to bind to the EGF receptor, become internalized, and inhibit protein synthesis was evaluated. A431 cells were exposed to DAB$_{389}$EGF for varying times and then labeled immediately to determine the percent of control protein synthesis. The cells were labeled with L-[2,3,4,5-3H]leucine for 1 h rather than the standard 2 h to minimize additional incubation time. The results of this experiment demonstrated that, within one hour, DAB$_{389}$EGF treatment reduced cellular protein synthesis by 50% and this inhibition was virtually complete by 4 h.

Specificity of DAB$_{389}$EGF Cytotoxicity

The assays described below demonstrate that a lupine synovial cell line is far more sensitive to intoxication by DAB$_{389}$EGF than are cell lines which express low levels of the EGF receptor.

All cells used in cytotoxicity assays were between passages 2 and 20 and were mycoplasma free. For toxicity assays, cells were plated in triplicate wells of 96 well plates in the presence of 100 μl of serial dilutions of DAB$_{389}$EGF in media. Following a 20 h incubation, protein synthesis was assayed by incubating the cells with L-[2,3,4,5-$^3$H]leucine, 5 μCi/ml (110 Ci/mmole; ICN) in leucine-free Minimum Essential Medium (GIBCO, Bethesda, Md.) for 2 h. Adherent cells were detached from the wells with 0.25% trypsin, 0.02% EDTA (JRH Biosciences, Lenexa, Ks.) and harvested onto glass fiber filter mats. Radioactivity was determined by liquid scintillation counting and expressed as a percent of the incorporation by control cells incubated in media alone. The IC$_{50}$ is the concentration of DAB$_{389}$EGF required to decrease radiolabel incorporation by 50% compared to cells incubated in media only.

Referring to Table 3, DAB$_{389}$EGF inhibited protein synthesis by a lupine synovial fibroblast cell line (HIG-82, American Type Culture Collection, Bethesda, Md., Accession No. CRL1832) by 50% at concentrations of $5\times10^{-10}$ to $5\times10^{-11}$M.

TABLE 3

Sensitivity of Various Cell Types to DAB$_{389}$EGF

| Cell Line | Tissue/Type | IC$_{50}$ | EGF Receptors/Cell |
|---|---|---|---|
| HIG-82 | synovial fibroblast | $1 \times 10^{-10}$ | $2 \times 10^4$ |
| A549 | lung carcinoma | $4 \times 10^{-11}$ | $2.8 \times 10^5$ |
| KB | oral epidermoid carcinoma | $4 \times 10^{-10}$ | $2.4 \times 10^5$ |
| SK BR3 | breast carcinoma | $8 \times 10^{-11}$ | $8.7 \times 10^4$ |
| A431 | vulval epidermoid carcinoma | $2 \times 10^{-12}$ | $1.5 \times 10^6$ |
| AAB527 | melonoma | $2 \times 10^{-10}$ | $1.0 \times 10^5$ |
| MCF-7 | breast adenocarcinoma | $4 \times 10^{-8}$ | $8 \times 10^2$ |
| A375 | malignant melanoma | $5 \times 10^{-8}$ | $4.4 \times 10^3$ |

The Effect of DAB$_{389}$EGF on Rat Adjuvant Arthritis

Chronic adjuvant arthritis is an autoimmune disease that can be experimentally induced in genetically susceptible rat strains by immunization with mycobacterial adjuvant. The disease is characterized by subacute polyarthritis involving the distal extremities which is similar clinically and pathologically to human rheumatoid arthritis. Similarities include synovitis, pannus formation, cartilage destruction and bone erosion (Holoshitz et al., Lancet, 2:305, 1986).

Adjuvant arthritis was induced in female Lewis rats (100 to 125 g; Harlan Sprague-Dawley Inc., Indianapolis, In.) by injecting a 10 mg/ml suspension of killed, dried Mycobacterium butyricum (Difco, Detroit, Mich.) in heavy mineral oil (Sigma Chemical Co., St. Louis, Mo.). One hundred microliters of the suspension was injected on day 0 intradermally at four to six sites on the lower back while animals were under light methoxyflurane anesthesia. Each rat was evaluated daily for clinical signs of arthritis. Severity of arthritis was quantified by scoring each paw on a scale of 0 to 4 which indicated the severity of peripheral joint swelling and erythema (0=no signs of disease, 1=disease evident in a small number of distal joints of a paw, 2=disease evident in all the distal joints of the paw, 3=disease evident in the entire paw and 4=severe disease evident in the entire paw (Trentham et al., J. Exp. Med.,146:857). The arthritic index was defined as the sum of the scores of all four paws for each animal with a maximal possible score of 16. Animals were scored by several different observers over the duration of each experiment.

Rats immunized with mycobacterial adjuvant typically develop signs of peripheral disease approximately on Day 10 post-immunization. The severity of swelling and erythema of the paws rapidly increases until Day 20 to 25, with A. Comparison of protein synthesis inhibition by DAB$_{389}$EGF and EGF. B. Comparison of protein synthesis inhibition between DAB$_{389}$EGF and two different concentrations of anti-EGF. C. Comparison of protein synthesis inhibition between DAB$_{389}$EGF and two different concentrations of anti-EGF receptor. individual arthritic indices as high as 10 to 14. Clinical symptoms then gradually decrease to a level which is approximately 50% of the peak by Day 40. Rats were randomly assigned to experimental groups (10 animals/group) were treated with DAB$_{389}$EGF in 0.01M phosphate (pH 7.5) 0.15M NaCl or buffer alone. Treatment occurred during the induction phase of the disease (Day 0 to 9) or was delayed (Days 6 to 15).

Daily subcutaneous administration of 0.1 mg/kg of DAB$_{389}$EGF from the day of adjuvant administration to Day 9 post-immunization markedly reduced the clinical features of the disease without producing any signs of systemic toxicity. Peak arthritis index was reduced 75% for animals treated on days 0 to 9 and 60% for animals treated on days 6 to 15.

Molecules Useful in the Method of the Invention

In general, there are three ways in which the EGF receptor targeted molecules useful in the invention can act: (1) the molecule can kill a cell by virtue of a cytotoxic domain; (2) the molecule (an antibody) can cause cell lysis by inducing complement fixation; or (3) the molecule can block binding or internalization of EGF. In all three cases the molecule must be targeted specifically to EGF receptor bearing cells; this is accomplished by including EGF (or an EGF receptor binding portion or derivative thereof) or an anti-EGF receptor antibody as part of the molecule.

Molecules useful for treating patients with inflammatory arthritis can thus take a variety of forms. When EGF itself is the targeting agent, the therapeutic molecule can be a cytotoxic hybrid molecule in which EGF is fused to a toxin molecule, preferably a polypeptide toxin. Derivatives of EGF which bind to EGF receptor, lack EGF activity and block binding and/or internalization EGF are useful in the method of the invention because they can prevent EGF-induced proliferation of EGF receptor bearing cells. When an anti-EGF antibody is the targeting agent, a cytotoxic hybrid molecule can be formed by fusing all or part of the antibody to a cytotoxin. The effectiveness of such an antibody/toxin hybrid, like that of an EGF toxin hybrid, depends on the hybrid molecule being taken up by cells to which it binds. Anti-EGF receptor antibodies which block binding and/or uptake of EGF are also useful in the method of the invention. Lytic anti-EGF antibodies are useful in the invention because they can cause complement-mediated lysis of EGF-bearing cells.

Transforming growth factor alpha (TGF-alpha) recognizes the EGF receptor and may also be used to target cells bearing the EGF receptor. The sequence of TGF-alpha is known, and some of the residues important for EGF receptor binding have been identified (Defeo-Jones et al., Molecular and Cellular Biology 8:2999, 1988).

Some of the molecules can be hybrid molecules formed by the fusion of all or part of two or more molecules. The hybrid molecule can be a hybrid protein encoded by a recombinant DNA molecule, in which case the two domains are joined (directly or through an intermediary domain) by a peptide bond. Alternatively, two domains can be produced separately and joined by a covalent bond in a separate chemical linkage step. In some cases, the cytotoxic domain of a hybrid molecule may itself be derived from two separate molecules.

Monoclonal Antibodies as Targeting Agents

Monoclonal antibodies directed against the EGF receptor of choice can be used to direct toxins to cells bearing that receptor. These antibodies or antibody fragments can be fused to a cytotoxin either by virtue of the toxin and the antibody being encoded by a fused gene which encodes a hybrid protein molecule, or by means of a non-peptide covalent bond which is used to join separately produced ligand and toxin molecules. Several useful toxins are described below.

Antibody/toxin hybrids can be tested for their ability to kill receptor bearing cells using a toxicity assay similar to that which is described above.

Toxins

The toxin molecules useful in the method of the invention are preferably toxins, such as peptide toxins, which are significantly cytotoxic only when present intracellularly. Of course, under these circumstances the molecule must be able to enter a cell bearing the targeted receptor. This ability depends on the nature of the molecule and the nature of the cell receptor. Cell receptors which naturally allow uptake of a ligand, for example EGF receptor, are likely to provide a means for a molecule which includes a toxin to enter a cell bearing that receptor. Preferably, a peptide toxin is fused to an EGF receptor binding domain by producing a recombinant DNA molecule which encodes a hybrid protein molecule. Such an approach ensures consistency of composition.

Many peptide toxins have a generalized eukaryotic receptor binding domain; in these instances the toxin must be modified to prevent intoxication of cells not bearing the targeted receptor (e.g., to prevent intoxication of cells not bearing the EGF receptor but having a receptor for the unmodified toxin). Any such modifications must be made in a manner which preserves the cytotoxic functions of the molecule (see U.S. Department of Health and Human Services, U.S. Ser. No. 401,412). Potentially useful toxins include, but are not limited to: cholera toxin, ricin, Shiga-like toxin (SLT-I, SLT-II, SLT-IIV), LT toxin, C3 toxin, Shiga toxin, pertussis toxin, tetanus toxin, Pseudomonas exotoxin, alorin, saporin, modeccin, and gelanin.

Diphtheria Toxin-based Molecules

As is evident from the examples described above, diphtheria toxin can be used to produce molecules useful in the method of the invention. Diphtheria toxin, whose sequence is known, is described in detail in Murphy U.S. Pat. No. 4,675,382, hereby incorporated by reference; the '382 patent also describes hybrid toxins of the general type described herein. The natural diphtheria toxin molecule secreted by Corynebacterium diphtheriae consists of several functional domains which can be characterized, starting at the amino terminal end of the molecule, as enzymatically-active Fragment A (amino acids Gly1—Arg193) and Fragment B (amino acids Ser194—Ser535), which includes a translocation domain and a generalized cell binding domain (amino acid residues 475 through 535).

The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotide - dependent adenosine diphosphate (ADP) ribosylation of the eukaryotic protein synthesis factor termed "Elongation Factor 2") causes the death of the intoxicated cell. It is apparent that a single molecule of Fragment A introduced into the cytosol is sufficient to inhibit the cell's protein synthesis machinery and kill the cell. The mechanism of cell killing by Pseudomonas exotoxin A, and possibly by certain other naturally-occurring toxins, is very similar.

Mixed Toxins

The cytotoxic portion of some molecules useful in the invention can be provided by a mixed toxin molecule. A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. The enzymatically active domain is the domain responsible for cytotoxic activity once the molecule is inside a cell.

Naturally-occurring proteins which are known to have a translocation domain include diphtheria toxin, Pseudomonas exotoxin A, and possibly other peptide toxins. The translocation domains of diphtheria toxin and Pseudomonas exotoxin A are well characterized (see, e.g., Hoch et al., Proc. Natl. Acad. Sci. USA 82:1692, 1985; Colombatti et al., J. Biol. Chem. 261:3030, 1986; and Deleers et al., FEBS Lett. 160:82, 1983), and the existence and location of such a domain in other molecules may be determined by methods such as those employed by Hwang et al. (Cell 48:129, 1987); and Gray et al. (Proc. Natl. Acad. Sci. USA 81:2645, 1984).

One useful mixed toxin hybrid molecule can be formed by fusing the enzymatically active A subunit of *E. coli* Shiga-like toxin (Calderwood et al., Proc. Natl. Acad. Sci. USA 84:4364, 1987) to the translocation domain (amino acid residues 202 through 460) of diphtheria toxin, and to EGF. The EGF portion of the three-part hybrid causes the molecule to attach specifically to EGF receptor-bearing cells, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell. The difference between these two types of hybrid toxins is the nature of their enzymatic activities: the enzymatic portion of $DAB_{486}EGF$ catalyzes the ADP-ribosylation by nicotinamide adenine dinucleotide of Elongation Factor 2, thereby inactivating this factor which is necessary for protein synthesis, while the enzymatic portion of the three part hybrid is a ribonuclease capable of cleaving ribosomal RNA at a critical site, thereby inactivating the ribosome. Three part hybrid would therefore be useful as a treatment for the same indications as $DAB_{389}EGF$, and could be substituted or used in conjunction with it if, for example, a patient's activated T-cells develop a resistance to $DAB_{389}EGF$.

Linkage of Toxins to Binding Ligands

The binding ligand and the cytotoxin of useful hybrid molecules can be linked in several ways. If the hybrid molecule is produced by expression of a fused gene, a peptide bond serves as the link between the cytotoxin and the binding ligand. Alternatively, the toxin and the binding ligand can be produced separately and later coupled by means of a non-peptide covalent bond.

For example, the covalent linkage may take the form of a disulfide bond. In this case, the DNA encoding EGF (or an EGF receptor targeted antibody) can be engineered to contain an extra cysteine codon. The cysteine must be positioned so as to not interfere with the EGF receptor binding activity of the molecule. The toxin molecule must be derivatized with a sulfhydryl group reactive with the cysteine of the modified EGF. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981). Derivatization can also be carried out according to the method described for the derivatization of a peptide hormone in Bacha et al. U.S. Pat. No. 4,468,382, hereby incorporated by reference. The introduction of sulfhydryl groups into proteins is described in Maasen et al. (Eur. J. Biochem. 134:32, 1983). Once the correct sulfhydryl groups are present, the cytotoxin and EGF receptor binding ligand are purified, both sulfur groups are reduced; cytotoxin and ligand are mixed; (in a ratio of about 1:5 to 1:20) and disulfide bond formation is allowed to proceed to completion (generally 20 to 30 minutes) at room temperature. The mixture is then dialyzed against phosphate buffered saline to remove unreacted ligand and toxin molecules. Sephadex chromatography or the like is then carried out to separate on the basis of size the desired toxin-ligand conjugates from toxin-toxin and ligand-ligand conjugates.

Assays for Toxicity

Molecules of the invention (both antibodies and hybrid molecules) can be screened for the ability to decrease viability of cells bearing the EGF receptor (e.g., HIG-68 cells) using the assay described above.

Therapy

Generally, the molecules of the invention will be administered by intravenous infusion. They may also be administered subcutaneously or injected directly into the inflamed joint. Dosages of molecules useful in the methods of the invention will vary, depending on factors such as whether the substance is a cytotoxin, a lytic antibody, or an EGF receptor blocking molecule. In the case of toxic molecules the extent of cell uptake is an important factor; less permeable molecules must be administered at a higher dose.

Other Embodiments

Other embodiments are within the following claims. The molecules described above act to decrease cell viability by directing a cytotoxin (or a lytic antibody) to cells bearing the EGF receptor. Also useful in the method of the invention are molecules which interfere with the targeted cell's ability to utilize EGF.

Derivatives of EGF which block utilization of endogenous EGF and which themselves do not have EGF activity are useful for preventing proliferation of targeted cells. Hybrid molecules in which the toxin has been rendered inactive can be also used to block the EGF receptor. A nontoxic mutant diphtheria toxin molecule has been described (Uchida et al. J. Biol. Chem. 248:3838, 1973), and this molecule might be used to produce a non-toxic EGF/diphtheria toxin hybrid. See Svrluga et al. U.S. Ser. No. 590,113, hereby incorporated by reference, for an example of such a hybrid molecule. In all cases it is essential that the molecule not possess significant EGF activity. Further, the molecule, by virtue of its affinity for the EGF receptor or its concentration relative to native EGF, must significantly compete with native EGF for binding to the EGF receptor.

Monoclonal antibodies can be used to kill or neutralize EGF receptor-bearing cells in a number of ways. As described above, anti-EGF receptor antibodies fused to a toxin molecule can be used to deliver the toxin to receptor-bearing cells. Lytic anti-EGF receptor antibodies can themselves kill EGF receptor-bearing cells by activating complement. For example, monoclonal antibodies which activate complement can be used to destroy EGF-bearing cells. Complement inducing antibodies are generally those of the IgG1, IgG2, IgG3, and IgM isotypes. Monoclonal anti-EGF receptor antibodies can be screened for those able to activate complement using a complement-dependent cytotoxicity test, as follows.

Also useful are antibodies which block binding and/or uptake of EGF. For example, monoclonal antibodies which interfere with the binding and/or uptake of EGF are useful in the method of the invention because EGF bearing cells deprived of EGF fail to proliferate. Blocking monoclonal antibodies (and other blocking molecules) can be tested for their ability to interfere with EGF bioactivity using the method. Generally, assays useful for blocking molecules will be competitive binding assays which measure the ability of the molecule being to interfere with binding of EGF.

Monoclonal antibodies useful in the method of the invention can be made by immunizing mice with human EGF bearing cells, fusing the murine splenocytes with appropriate myeloma cells, and screening the antibodies produced by the resultant hybridoma lines for the requisite EGF receptor binding properties by means of an ELISA assay. Antibody production and screening can be performed according to Uchiyama et al. (J. Immunol. 126:1393, 1981). Alternatively, useful antibodies may be isolated from a combinatorial library produced by the method of Huse et al. (Science 246:1275, 1989).

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or a chimeric antibody, for example, an antibody which contains the binding specificity of a murine antibody, but in which the remaining portions are of human origin.

What is claimed is:

1. A method for treating a patient having an inflammatory arthritis characterized by higher than normal expression of the epidermal growth factor receptor on synovial fibroblasts, said method comprising administering to said patient a hybrid molecule comprising a first portion and a second portion joined together covalently, said first portion comprising fragment A of diphtheria toxin and enough of fragment B of diphtheria toxin to facilitate entry of said hybrid molecule into the cytosol of a cell to which said hybrid molecule binds, said second portion comprising all or an epidermal growth factor receptor-binding portion of epidermal growth factor.

2. The method of claim 1 wherein said hybrid molecule is $DAB_{389}EGF$.

3. The method of claim 1 wherein said hybrid molecule is $DAB_{486}EGF$.

4. A method for treating a patient having an inflammatory arthritis characterized by higher than normal expression of the epidermal growth factor receptor on synovial fibroblasts, said method comprising administering to said patient a hybrid molecule comprising a first portion and a second portion joined together covalently, said first portion comprising fragment A of diphtheria toxin and enough of fragment B of diphtheria toxin to facilitate entry of said hybrid molecule into the cytosol of a cell to which said hybrid molecule binds, said second portion comprising all or an epidermal growth factor receptor-binding portion of tissue growth factor alpha.

5. The method of claim 4 wherein said hybrid molecule is $DAB_{389}$TGF-alpha.

6. The method of claim 4 wherein said hybrid molecule is $DAB_{486}$TGF-alpha.

7. The method of claim 1 or 4 wherein said inflammatory arthritis is systemic lupus-associated arthritis.

8. The method of claim 1 or 4 wherein said inflammatory arthritis is psoriatic arthritis.

9. A method for treating a patient having rheumatoid arthritis, said method comprising administering to said patient a hybrid molecule comprising a first portion and a second portion joined together covalently, said first portion comprising fragment A of diphtheria toxin and enough of fragment B of diphtheria toxin to facilitate entry of said hybrid molecule into the cytosol of a cell to which said hybrid molecule binds, said second portion comprising all or an epidermal growth factor receptor-binding portion of epidermal growth factor.

10. The method of claim 9 wherein said hybrid molecule is $DAB_{389}EGF$.

11. The method of claim 9 wherein said hybrid molecule is $DAB_{486}EGF$.

12. A method for treating a patient having rheumatoid arthritis, said method comprising administering to said patient a hybrid molecule comprising a first portion and a second portion joined together covalently, said first portion comprising fragment A of diphtheria toxin and enough of fragment B of diphtheria toxin to facilitate entry of said hybrid molecule into the cytosol of a cell to which said hybrid molecule binds, said second portion comprising all or an epidermal growth factor receptor-binding portion of tissue growth factor.

13. The method of claim 11 wherein said hybrid molecule is $DAB_{389}$TGF-alpha.

14. The method of claim 12 wherein said hybrid molecule is $DAB_{486}$TGF-alpha.

* * * * *